United States Patent [19]

Busse et al.

[11] 4,451,475

[45] May 29, 1984

[54] CYCLIC SULPHENAMIDE COMPOUNDS, THEIR PRODUCTION AND THEIR MEDICINAL USE

[75] Inventors: Wolf-Dieter Busse, Wuppertal; Edmund Krauthausen, Cologne; Mithat Mardin, Wuppertal, all of Fed. Rep. of Germany

[73] Assignee: Bayer Aktiengesellschaft, Leverkusen, Fed. Rep. of Germany

[21] Appl. No.: 368,329

[22] Filed: Apr. 14, 1982

[30] Foreign Application Priority Data

May 7, 1981 [DE] Fed. Rep. of Germany ....... 3118129

[51] Int. Cl.³ .................. C07D 263/22; C07D 277/14; A61K 31/42; A61K 31/425
[52] U.S. Cl. ..................................... 424/270; 424/272; 548/147; 548/165; 548/182; 548/183; 548/184; 548/216; 548/221; 548/225; 548/226; 548/229
[58] Field of Search ............... 548/183, 182, 221, 229, 548/184, 147, 165, 216, 225, 226; 424/770, 272

[56] References Cited

U.S. PATENT DOCUMENTS 3,249,620  5/1966  Kuhle ................................. 548/221
3,285,929  11/1966  Klauke ............................... 548/183
4,165,417  8/1979  Wolfinger .......................... 548/183

*Primary Examiner*—Robert Gerstl
*Attorney, Agent, or Firm*—Sprung, Horn, Kramer & Woods

[57] ABSTRACT

The invention relates to cyclic sulphenamides of Formula I and methods for their manufacture. Also included in the invention are compositions containing said cyclic sulphenamides and methods for the use of said compounds and compositions as lipoxygenase inhibitors.

18 Claims, No Drawings

CYCLIC SULPHENAMIDE COMPOUNDS, THEIR PRODUCTION AND THEIR MEDICINAL USE

The present invention relates to certain new sulphenamide compounds, to a process for their production and to their use as lipoxygenase inhibitors.

It is known that the metabolites of arachidonic acid which are formed by the enzyme lipoxygenase are involved in the development of inflammatory and allergic processes (see E. J. Goetzl, Immunology 40, 709 (1980); Ford-Hutchinson et al., J. Pharm. Pharmacol. 32, 517 (1980) and Nature 286, 264 (1980); Samuelsson, Trends in Pharmacol. Sci., May 1980, 227; and Borgeat et al., J. Med. Chem. 24, 121 (1981)).

Known inhibitors of lipoxygenase, such as nordihydroguaiaretic acid, 3-amino-1-(3-trifluoromethylphenyl)-pyrazoline, phenidone and 5,8,11,14-eicosatetraenoic acid are either simultaneously inhibitors of cyclooxygenase or only active at very high concentrations. The inhibition of the enzyme cyclooxygenase of the metabolism of arachidonic acid leads to a global inhibition of the synthesis of prostaglandins and to a stimulation of the lipoxygenase route, which causes gastrotoxicity or pro-inflammatory and asthmatic effects (see Yen and Kreutner, Agents and Actions, 10, 274 (1980) and Blackwell and Flower, Prostaglandins 16, 417 (1978); and see also Brune et al., J. Pharm. Pharmacol. 33, 127–128 (1981); Higgs et al., Eur. J. Pharmacol. 66, 81–86 (1980) and Piper et al., Prostaglandins 19, 371 (1980)). There is a pressing need for compounds which do not have these undesirable side-effects.

Surprisingly, the sulphenamides according to the invention inhibit the lipoxygenase very specifically, even at those concentrations at which cyclooxygenase is not influenced. This very strong and specific effect of the sulphenamides could not be expected from knowledge of the state of the art. The sulphenamides according to the invention which inhibit lipoxygenase can therefore be used as medicaments for the treatment of inflammatory and allergic processes. They can be employed, in particular, as antiphlogistic, antirheumatic, antiatherosclerotic, antiasthmatic, antiallergic, antimetastatic and gastroprotective agents.

According to the present invention there are provided compounds which are sulphenamides corresponding to the formula

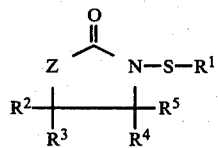

(I)

wherein
Z denotes oxygen or sulphur;
$R^1$ represents a radical of the formula

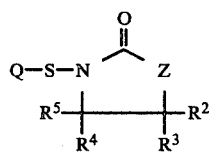

(Ia)

wherein
Z has the above-mentioned meaning and
$R^2$ to $R^5$ have the meanings given below, and
Q represents an alkylene radical with 1 to 12 (especially 1 to 6) carbon atoms, in which the alkylene radical is optionally interrupted by one or more oxygen, sulphur or nitrogen atoms, or represents a cycloalkylene radical with 5 to 12 (preferably 5 to 6) carbon atoms, arylene (preferably mono- or bi-cyclic carbocylic arylene) with 6 to 10 carbon atoms or an alkylene-cycloalkylene-alkylene or alkylene-arylene-alkylene radical in which each alkylene group contains 1 to 12 carbon atoms, each cycloalkylene group 5 to 12 carbon atoms and each arylene group is mono- or bi-cyclic carbocyclic arylene, or
$R^1$ represents an alkyl group with 1 to 18 (especially 1 to 6) carbon atoms, an alkenyl or alkynyl group with 2 to 12 (especially 2 to 6) carbon atoms, an aralkyl group with 7 to 12 carbon atoms (especially mono- or bi-cyclic carbocyclic aryl-$C_1$-$C_2$-alkyl), a cycloalkyl group with 5 to 8 (especially 5 to 6) carbon atoms or an aryl group with 6 to 14 carbon atoms (especially mono-, bi, or tri-cyclic carbocyclic aryl); each of the above-mentioned groups optionally being substituted by up to 5 (especially 1 or 2) identical or different substitutents selected from alkoxy, alkyl, aralkyl, cycloalkyl, aryl, aryloxy, arylthio, alkylthio, carboxyl, carbalkoxy, cyano, carbamoyl, sulphonyl, halogenoalkyl, halogenoalkoxy, halogen, amino and substituted amino, and
each $R^2$ to $R^5$ represent, independently of each other, a hydrogen atom, an optionally substituted alkyl group with 1 to 8 carbon atoms, a cycloalkyl group with 5 to 8 carbon atoms, an aralkyl group with 7 to 12 carbon atoms, an aryl group with 6 or 10 carbon atoms, an alkoxy group with 1 to 12 carbon atoms, an aralkoxy group with 7 to 10 carbon atoms, an aryloxy group with 6 or 10 carbon atoms, an alkylthio group with 1 to 12 carbon atoms, a benzylthio group, an arylthio group with 6 or 10 carbon atoms, or an amino group which is substituted by alkyl, benzyl and/or aryl (it being possible for the alkyl substituent(s) of the amino group to contain 1 to 8 carbon atoms and for the aryl substituent(s) of the amino group to contain 6 or 10 carbon atoms), or
$R^2$ together with $R^4$ forms a direct bond or an alkylene radical with 3 to 6 carbon atoms, or
$R^2$ and $R^3$ together represent an alkylidene radical with 1 to 4 carbon atoms, an aralkylidene radical with 7 to 10 carbon atoms, or an oxo, thiono or substituted imino radical, or the radicals $R^2$ and $R^3$, together with the carbon atoms to which they are bonded, form a cycloalkyl radical with 5 to 8 ring members, or
$R^4$ and $R^5$ together represent an alkylidene radical with 1 to 4 carbon atoms, an aralkylidene radical with 7 to 10 carbon atoms, or an oxo or substituted imino radical, or
the radicals $R^4$ and $R^5$ or $R^2$ and $R^3$, together with the carbon to which they are bonded, form a cycloalkyl radical with 5 to 8 ring members, or
the radicals $R^2$ to $R^5$, together with the carbon atoms to which they are bonded, form an optionally substituted, fused-on benzene ring.

Unless otherwise indicated as used herein, the term "alkyl", "alkoxy", "alkylthio" and "carbalkoxy" means especially substituents containing 1 to 12 (preferably 1 to 4) carbon atoms; the term "aralkyl" means especially mono- or bi-cyclic carbocyclic aryl -$C_1$-$C_2$-alkyl; the term "cycloalkyl" means especially a substitutent having 4 to 12 (particularly 5 or 6) carbon atoms; the terms "aryl", "aryloxy" and "arylthio" meand especially mono- or bi-cyclic carbocyclic aryl moieties; "halogenoalkyl" and "halogenoalkoxy" mean especially substitutents containing 1 to 4 (particularly 1 to 2) carbon atoms and 1 to 5 halogen (particularly chlorine or fluorine) atoms to most preferably provide perhalo alkyl or alkoxy (particularly perfluoro alkyl or alkoxy) substituents; substituted amino means especially mono- or bi-$C_1$-$C_4$-alkyl.

Preferred compounds according to the present invention are those in which

Z has the abovementioned meaning, $R^1$ represents an alkyl group with 1 to 18 carbon atoms, a cycloalkyl group with 5 to 8 carbon atoms or an aryl group with 6 to 14 carbon atoms; each of the abovementioned groups optionally being substituted by up to 5 identical or different substituents selected from alkyl and alkoxy with in each case 1 to 4 carbon atoms, aralkyl with 7 to 10 carbon atoms, cycloalkyl with 5 to 7 carbon atoms, phenyl, phenoxy, phenylthio, alkylthio with 1 to 4 carbon atoms, carboxyl, carbalkoxy with 1 to 4 carbon atoms, cyano, trifluoromethyl, trifluoromethoxy, fluorine, chlorine, bromine, amino, alkyl-substituted amino and benzyl-substituted amino, the alkyl substituent(s) of amino carrying 1 to 4 carbon atoms, and $R^2$ to $R^5$ represents, independently of one another, a hydrogen atom, an alkyl group with 1 to 4 carbon atoms or a phenyl group, or $R^2$ forms a direct bond with $R^4$, or $R^2$ and $R^3$, or $R^4$ and $R^5$ together represent an oxo group, Particularly preferred compounds according to the present invention are those in which Z represents oxygen $R^1$ represents an aryl radical which has 6 or 10 carbon atoms and is optionally substituted by 1 or 2 identical or different substituents selected from alkyl and alkoxy with in each case 1 to 4 carbon atoms, aralkyl with 7 to 10 carbon atoms, cycloalkyl with 5 to 7 carbon atoms, phenyl, phenoxy, phenylthio, alkylthio with 1 to 4 carbon atoms, carbalkoxy with 1 to 4 carbon atoms, cyano, trifluoromethyl, trifluoromethoxy, fluorine, chlorine, bromine, alkyl-substituted amino and benzyl-substituted amino, the alkyl substituent(s) of amino carrying 1 to 4 carbon atoms and $R^2$ to $R^5$ represent, independently of one another, a methyl group or a hydrogen atom.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

According to the present invention there is further provided a process for the production of a compound of the present invention, in which a sulphenyl halide of the formula

$$R^1-S-X \quad (II)$$

wherein $R^1$ has the abovementioned meaning and

X represents a chlorine, bromine or iodine atom (preferably a chlorine atom), is reacted with a cyclic compound of the formula

(III)

wherein

Z and $R^2$ to $R^5$ have the abovementioned meaning and

Y represents a hydrogen atom, a trialkylsilyl group, a metal (such as K, Na, Li, Mg, Ca, Ba, Ag, Cu, Zn, Fe, Mn, Pb, Sn or Al), or an ammonium radical, X-Y being split off.

For the case where Y denotes a hydrogen atom, it is advantageous to carry out the reaction in the presence of a base. Bases which may be mentioned as preferred are organic compounds such as triethylamine, tributylamine, benzyldimethylamine, dimethylaniline, pyridine or quinoline.

The reaction according to the present invention is preferably carried out in the presence of an aprotic solvent (such as hexane, ligroin, toluene, chlorobenzene, chloroform, carbon tetrachloride, dimethylsulphoxide or dimethylformamide).

For the case where Y does not represent a trialkylsilyl group, it can be advantageous to carry out the preparation in an aqueous organic two-phase medium. In this case, an inorganic base (such as an alkali metal or alkaline earth metal hydroxide or carbonate) can also be employed to take up hydrogen halide.

The reaction is generally carried out at a temperature between $-80°$ and $+150°$ C., preferably between $0°$ and $50°$ C.

Suitable amines of the formula (III) for carrying out the invention are known or can be prepared according to known methods (see R. C. Elderfield (Ed.), Heterocyclic Compounds, volume 5, pages 396 et seq., 405 et seq. and 711 et seq., J. Wiley & Sons, New York 1957; and Cook et al., J. Chem. Soc. 1949, 2,367).

Suitable sulphenyl halides of the formula (II) for carrying out the invention are known or can also be prepared by known methods (see E. Kühle, The Chemistry of the Sulfenic Acids, G. Thieme Verlag, Stuttgart 1973, pages 2 to 37).

Examples of compounds according to the present invention are:

3-phenylthio-oxazolidin-2-one, 3-(4-chlorophenylthio)-oxazolidin-2-one, 3-(4-tert.-butylphenylthio)-oxazolidin-2-one, 3-pentachlorophenylthio-oxazolidin-2-one, 3-cyclohexylthio-oxazolidin-2-one, 3-isopropylthio-oxazolidin-2-one, 3-naphthylthio-oxazolidin-2-one, 3-(4-methylphenylthio)-oxazolidin-2-one, 3-(3-trifluoromethyl-4-chlorophenylthio)-oxazolidin-2-one, 3-(2-carbomethoxyphenylthio)-thiazolidin-2-one, 9-phenylthio-9-aza-8-oxo-7-oxo-spiro-[5,4]-decane, 5-benzylidene-3-(3,4-dichlorophenylthio)-4-thiono-oxazolidine-2-one, 5,5-dimethyl-3-tert.-butylthio-oxazolidin-2,4-dione, 5-isopropylidene-4-phenyl-3-phenylthio-oxazolidin-2-one, 3-benzylthio-$\Delta^4$-oxazolin-2-one, 4-benzylidene-3-(4-ethoxyphenylthio)-oxazolidin-2-one, 3-phenylthiobenzothiazolin-2-3H-one, 3-(3-chloro-4-nitrophenylthio)-4,4-dimethyl-thiazolidin-2-one, 3-(4-fluorophenylthio)benzoazolin-2-one, 3-(4-chlorophenylthio)-4-phenylthiazolin-2-one and 3-(4-fluorophenylthio)-oxazolidin-2-one.

The lipoxygenase-inhibitory properties of the sulphenamides are demonstrated by a method analogous to that of Bailey et al., J. Biol. Chem. 255, 5,996, (1980) and according to Blackwell and Flower, Prostaglandins 16, 417 (1978). Use is made in this test method of the metabolism of radioactively labelled arachidonic acid by washed human platelets. In this in vitro test, the radioactively labelled metabolites are extracted from the reaction mixture and separated by thin layer chromatography. The autoradiogram is evaluated on a thin layer scanner. Under these test conditions, the labelled metabolites are separated from the unreacted arachidonic acid and are subsequently quantitatively evaluated. The distribution of the radioactivity in the cyclooxygenase products, formed during metabolism, thromboxane $B_2$ ($TXB_2$) and 12-hydroxy-5,8,10-heptadecatrienoic acid (HHT) and the lipoxygenase product 12-hydroxy-5,8,11,14-eicosatetraenoic acid (HETE), as influenced by the inhibitors, gives a measure of the inhibition of the enzymes.

The inhibition of lipoxygenase by the sulphenamides according to the invention can be measured by the inhibition of the synthesis of HETE. It is found that the synthesis of $TXB_2$ and of HHT are unaffected, whilst the conversion of arachidonic acid decreases. As can be seen the following table, the sulphenamides bring about a significant inhibition of the platelet lipoxygenase (synthesis of HETE).

| Inhibition of the platelet lipoxygenase (synthesis of HETE) | |
|---|---|
| Compound from Example No. (see below) | Minimum effective inhibitory concentration (g/ml) (at least 50% inhibition) |
| 2 | $10^{-6}$ |
| 4 | $10^{-7}$ |
| 5 | $3 \times 10^7$ |

The sulphenamides according to the present invention are also active in vivo. This activity is demonstrated by methods which are in themselves known, by measurement of the inhibition of the migration of leucocytes (compare Higgs et al., Biochemical Pharmacology 28, 1,959 (1979) and Eur. J. Pharmacol. 66, 81 (1980)). The following Table 2 summarises the activities of some illustrative sulphenamides after local administration, by introduction of a piece of sponge soaked in the active compound under the dorsal skin of rats.

| Compound No. | Dose, local (mg/rat) | Inhibition of the migration of leucocytes (control = 0%) |
|---|---|---|
| 2 | 10 | 55% |
| 4 | 10 | 80% |
| 5 | 10 | 72% |
| 10 | 10 | 53% |

The antiasthmatic activity of the compound according to the invention can also be demonstrated by methods which are already known (compared Samuelson et al., FEBS Letters, 110, 213 (1980) and Yen et al., Agents and Actions 10, 274 (1980)).

As stated above, the invention also relates to the use in medicine for combating inflammatory or allergic processes of the compounds of the invention.

The present invention provides a pharmaceutical composition containing as active ingredient a compound of the invention in admixture with an inert solvent, i.e. a solid or liquefied gaseous diluent, or in admixture with a liquid diluent other than solvent of a molecular weight-less than 200 (preferably less than 350) except in the presence of a surface active agent.

The invention further provides a pharmaceutical composition containing as active ingredient a compound of the invention in the form of a sterile-and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and soild polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated for together with one or several of the abovement-oned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, or course, the above-mentioned exclusion of solvents having a molecular weight below 200 except in the presence of a surface-active agent), such as solvents, dissolving agents and emulsifiers; specific examples of such diluents are water, ethyl alcohol, isopropyl-alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for intravenous administration of the medicaments of the invention is 2.5 to 250 mg of active ingredient and for oral administration of the medicaments of the invention is 5 to 500 mg of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially perlingually or intravenously. Preferred pharmaceutical compositions and medicaments are therefore those adapted for administration such as oral or parenteral administration. Administration in the method of the invention is preferably oral or parenteral administration.

In general it has proved advantageous to administer intravenously amounts of from 0.01 to 10 mg/kg, preferably 0.05 to 5 mg/kg, of body weight per day or to administer orally amounts of from 0.05 to 100 mg/kg, preferably 0.1 to 10 mg/kg, of body weight per day, to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst-other cases the upper limit mentioned must be exceeded to achieve the desired results. Where larger amounts are administered it can be advisable to divide these into several individual administrations over the course of the day.

The following Examples illustrate the production of compounds of the invention in more detail.

EXAMPLE 1

A solution of 0.6 mol of 2-propylsulphenyl chloride in 200 ml of chlorobenzene was added dropwise at 0° to 10° C. to 52.2 g (0.6 mol) of oxazolidin-2-one and 85 g (0.62 mol) of dimethylbenzylamine in 200 ml of chlorobenzene and 50 ml of dimethylformamide. After stirring for 1.5 hours at room temperature, the mother liquor was filtered from precipitated amine hydrochloride, washed with water and dried over sodium sulphate and the solvent was subsequently removed in vacuo at 40° C. 58 g of 3-(2-propylthio)oxazolidin-2-one were obtained as a brown oil.

$^1$H-NMR (CDCl$_3$): $\delta$=1.27 (d, J=7 Hz, 6H); 3.43 (heptet, J=7 Hz, 1H) and 3.65-4.6 ppm (m, AA'BB' system, 4H).

EXAMPLE 2

Analogously to Example 1, 51.5 g of 3-phenylthio-oxazolidin-2-one were obtained as a brown oil from 0.6 mol of phenylsulphenyl chloride and oxazolidin-2-one.

$^1$H-NMR (CDCl$_3$): $\delta$=3.55-4.5 (m, AA'BB' system, 4H) and 7.32 ppm (symmetrical m, 5H).

EXAMPLE 3

Analogously to Example 1, 100 g of 3-pentachlorophenylthio-oxazolidin-2-one with a melting point of 195°-7° C. were obtained from pentachlorophenyl-sulphenyl chloride and oxazolidin-2-one.

EXAMPLE 4

Analogously to Example 1, 5 g of 3-(4-chlorophenyl-thio)-oxazolidin-2-one were obtained as a colourless powder with a melting point of 65° to 70° C. from 0.025 mol of 4-chlorophenylsulphenyl chloride in 100 ml of toluene and 2.2 g (0.025 mol) of oxazolidin-2-one in 20 ml of dimethylformamide.

EXAMPLE 5

Analogously to Example 4, 2.7 g of 3-(4-tert.-butyl-phenylthio)-oxazolidin-2-one were obtained as colourless crystals with a melting point of 76° to 81° C. from 4-tert.-butylphenylsulphenyl chloride and oxazolidin-2-one.

EXAMPLE 6

Analogously to Example 4, 33% yield of 3-(4-chlorophenylthio)-5-phenoxymethyloxazolidin-2-one with a melting point of 98° to 101° C. was obtained from 4-chlorophenylsulphenyl chloride and 5-phenoxyme-thyloxazolidin-2-one.

EXAMPLE 7

Analogously to Example 4, 3-(4-fluorophenylthio)ox-azolidin-2-one was obtained as a pale yellow oil from 4-fluorophenylsulphenyl chloride and oxazolidin-2-one. $^1$H-NMR and mass spectrum were in agreement with the structure given.

Analogously to Example 4, 4-chlorophenylsulphenyl chloride was added dropwise to the heterocycles as indicated in the following Examples.

EXAMPLE 8

62% yield of 3-(4-chlorophenylthio)-benzoxazolin-2-one with a melting point of 134° to 137° C. was obtained from benzoxazolin-2-one.

EXAMPLE 9

3-(4-chlorophenylthio)-4,4-dimethyloxazolidin-2-one with a melting point of 124° to 126° C. was obtained from 4,4-dimethyloxazolidin-2-one.

EXAMPLE 10

69% yield of 3-(4-chlorophenylthio)-4-phenylthiazo-lin-2-one with a melting point of 205° to 207° C. was obtained from 4-phenyl-4-thiazolin-2-one.

EXAMPLE 11

80% yield of 3-(4-chlorophenylthio)-5-phenylox-azolidin-2-one with a melting point of 98° to 99° C. was obtained from 5-phenyloxazolidin-2-one.

EXAMPLE 12

77% yield of 3-(4-chlorophenylthio)-thiazolidin-2,4-dione as brownish-yellow oil was obtained from thiazolidin-2,4-dione. The mass spectrum was in agreement with the structure given.

EXAMPLE 13

92% yield of 3-(4-chlorophenylthio)-3a,4,5,6,7,7a-hexahydrobenzoxazolin-2-one as viscous yellow oil was obtained from 3a,4,5,6,7,7a-hexahydrobenzoxazolin-2-one. The mass spectrum was in agreement with the structure given.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound which is a sulphenamides of the formula

wherein

Z denotes oxygen or sulphur,

R$^1$ represents a radical of the general formula

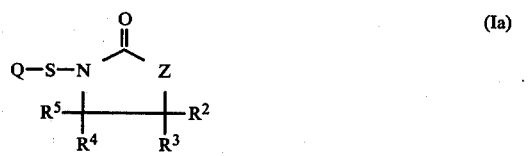

wherein

Z has the abovementioned meaning and

R$^1$ to R$^5$ have the meanings given below, and

Q represents an alkylene radical with 1 to 12 carbon atoms, in which the alkylene radical is optionally interrupted by one or more oxygen, sulphur or nitrogen atoms, or represents a cycloalkylene radical with 5 to 12 carbon atoms, arylene with 6 to 10 carbon atoms or an alkylene-cyclo-alkylene-alkylene or alkylene-arylene-alkylene radical, or $R^1$ represents an alkenyl or alkynyl group with 2 to 12 carbon atoms, an aralkyl group with 7 to 11 carbon atoms, a cycloalkyl group with 5 to 8 carbon atoms or an aryl group with 6 to 14 carbon atoms; each of the abovementioned groups optionally being substituted by up to 5 identical or different substituents selected from alkoxy, alkyl, aralkyl, cycloalkyl, aryl, aryloxy, arylthio, alkylthio, carboxyl, carbalkoxy, cyano, carbamoyl, sulphonyl, halogenoalkyl, halogenoalkoxy, halogen, amino and amino by $C_1$-$C_4$-alkyl or benzyl, and each $R^2$ and $R^5$ represent, independently of each other, a hydrogen atom, an alkyl group with 1 to 8 carbon atoms, a cycloalkyl group, with 5 to 8 carbon atoms, an aralkyl group with 7 to 10 carbon atoms, an aryl group with 6 or 10 carbon atoms, an alkoxy group with 1 to 12 carbon atoms, an aralkoxy group with 7 to 10 carbon atoms, an aryloxy group with 6 or 10 carbon atoms, an alkylthio group with 1 to 12 carbon atoms, a benzylthio group, an arylthio group with 6 or 10 carbon atoms, or an amino group which is substituted by alkyl, benzyl and/or aryl, or $R^2$ together with $R^4$ forms a direct bond or an alkylene radical with 3 to 6 carbon atoms, or $R^2$ and $R^3$ together represent an alkylidene radical with 1 to 4 carbon atoms, an aralkylidene radical with 7 to 10 carbon atoms, or an oxo, thiono or imino radical, or the radicals $R^2$ and $R^3$, together with the carbon atoms to which they are bonded, form a cycloalkyl radical with 5 to 8 ring members, or $R^4$ and $R^5$ together represent an alkylidene radical with 1 to 4 carbon atoms, an aralkylidene radical with 7 to 10 carbon atoms, or an oxo or imino radical, or the radicals $R^4$ and $R^5$ or $R^2$ and $R^3$, together with the carbon atom to which they are bonded, form a cycloalkyl radical with 5 to 8 ring members, or the radicals $R^2$ to $R^5$, together with the carbon atoms to which they are bonded, form an, fused-on benzene ring.

2. A compound according to claim 1, in which $R^2$ to $R^5$ have the same meaning as in claim 1, except that $R^2$ to $R^5$, together with the carbon atoms to which they are bonded do not form the, fused-on benzene ring.

3. A compound according to claim 1, in which
Z has the same meaning as in claim 1,
$R^1$ represents a cycloalkyl group with 5 to 8 carbon atoms or an aryl group with 6 to 14 carbon atoms; each of the abovementioned groups optionally being substituted by up to 5 identical or different substituents selected from alkyl and alkoxy with in each case 1 to 4 carbon atoms, aralkyl with 7 to 10 carbon atoms, cycloalkyl with 5 to 7 carbon atoms, phenyl, phenoxy, phenylthio, alkylthio with 1 to 4 carbon atoms, carboxyl, carbalkoxy with 1 to 4 carbon atoms, cyano, trifluoromethyl, trifluoromethoxy, fluorine, chlorine, bromine, amino, alkyl-substituted amino and benzyl-substituted amino, the alkyl substituent(s) of amino carrying 1 to 4 carbon atoms, and $R^2$ to $R^5$ represents, independently of one another, a hydrogen atom, an alkyl group with 1 to 4 carbon atoms or a phenyl group, or $R^2$ forms a direct bond with $R^4$, or $R^2$ and $R^3$, or $R^4$ and $R^5$ together represent an oxo group.

4. A compound according to claim 1 in which
Z represents oxygen
$R^1$ represents an aryl radical which has 6 or 10 carbon atoms and is optionally substituted by 1 or 2 identical or different substituents selected from alkyl and alkoxy with in each case 1 to 4 carbon atoms, aralkyl with 7 to 10 carbon atoms, cycloalkyl with 5 to 7 carbon atoms, phenyl, phenoxy, phenylthio, alkylthio with 1 to 4 carbon atoms, carbalkoxy with 1 to 4 carbon atoms, cyano, trifluoromethyl, trifluoromethoxy, fluorine, chlorine, bromine, alkyl-substituted amino and benzyl-substituted amino, the alkyl substituent(s) of amino carrying 1 to 4 carbon atoms and $R^2$ to $R^5$ represent, independently of one another, a methyl group or a hydrogen atom.

5. A compound of claim 1 which is 3-phenylithooxazolidin-2-one.

6. A compound of claim 1 which is 3-(4-chlorophenoxythio)-oxazolidin-2-one.

7. A compound of claim 1 which is 3-(4-tert.-butylphenylthio)-oxazolidin-2-one.

8. A compound of claim 1 which is 3-(4-fluorophenylthio)-oxazolidin-2-one.

9. A compound of claim 1 which is 3-(4-chlorophenylthio)-4-phenyl-thiazolin-2-one.

10. A compound of claim 1 which is 3-(4-fluorophenylthio)-benzoxazolin-2-one.

11. A pharmaceutical composition containing as an active ingredient a compound according to claim 1 in admixture with an inert pharmaceutical carrier.

12. A pharmaceutical composition of claim 11 containing as an active ingredient a compound according to claim 1 in admixture with an inert pharmaceutical carrier in the form of a steril or physiologically isotonic aqueous solution.

13. A composition according to claim 11 or 12 containing from 0.5 to 95% by weight of the said active ingredient.

14. A medicament in dosage unit form comprising a lipoxygenase-inhibiting amount of a compound according to claim 1.

15. A medicament of claim 14 in the form of tablets, pills, dragees, capsules, ampoules, or suppositories.

16. A method of combating inflammatory or allergic processes in warm-blooded animals which comprises administering to the animals a active compound according to claim 1 either alone or in admixture with a diluent or in the form of a medicament.

17. A method according to claim 16 in which the active compound is administered intravenously in an amount of 0.01 to 10 mg per kg body weight per day.

18. A method according to claim 16 in which the active compound is administered orally in an amount of 0.05 to 100 mg per kg body weight per day.

* * * * *